United States Patent [19]

Keilman et al.

[11] Patent Number: 4,568,345

[45] Date of Patent: Feb. 4, 1986

[54] CONTAINER AND ASSOCIATED CAP ASSEMBLY FOR PLASMA COLLECTION AND THE LIKE

[75] Inventors: Michael R. Keilman, Mundelein; Richard L. West, Ingleside, both of Ill.

[73] Assignee: Baxter Travenol Laboratories, Inc., Deerfield, Ill.

[21] Appl. No.: 534,476

[22] Filed: Sep. 21, 1983

Related U.S. Application Data

[63] Continuation-in-part of Ser. No. 417,728, Sep. 13, 1982, abandoned.

[51] Int. Cl.[4] .......................... A61M 5/00; A61J 1/00

[52] U.S. Cl. .................................... 604/403; 215/309

[58] Field of Search ........................ 604/405, 403, 408; 128/DIG. 24; 222/206, 530; 150/248, 1 C; 215/306, 308, 309, 228, 100 R

[56] References Cited

U.S. PATENT DOCUMENTS

| | | | |
|---|---|---|---|
| D. 255,872 | 7/1980 | Shrine et al. . | |
| D. 266,017 | 8/1982 | Kellogg . | |
| D. 271,804 | 12/1983 | Momoda | D24/56 |
| 596,158 | 12/1897 | Harris . | |
| 2,138,936 | 12/1938 | Osterberg . | |
| 2,744,661 | 5/1956 | Davis . | |
| 2,770,234 | 11/1956 | Nessett et al. . | |
| 2,789,734 | 4/1957 | Biederman . | |
| 2,844,267 | 7/1958 | Petriccione . | |
| 2,957,614 | 10/1960 | Krajovic . | |
| 3,059,816 | 10/1962 | Goldstein . | |
| 3,103,335 | 9/1963 | Martinez . | |
| 3,160,330 | 12/1964 | Pollitt . | |
| 3,217,928 | 11/1965 | Burbig . | |
| 3,537,456 | 11/1970 | Harautuneian . | |
| 3,638,834 | 2/1972 | Goodrich et al. . | |
| 3,724,461 | 4/1973 | Eisenberg . | |
| 3,863,817 | 2/1975 | Speaker . | |
| 3,939,623 | 2/1976 | Shrine et al. . | |
| 3,952,902 | 4/1976 | Prouty et al. . | |
| 3,957,168 | 5/1976 | Shrine et al. . | |
| 3,980,210 | 9/1976 | Kligerman . | |
| 4,080,989 | 3/1978 | Chapelsky et al. . | |
| 4,153,173 | 5/1979 | Ward et al. . | |
| 4,234,095 | 11/1980 | Safianoff . | |
| 4,236,655 | 12/1980 | Humphries . | |
| 4,307,766 | 12/1981 | Tanokura . | |

OTHER PUBLICATIONS

Brochure on PLASMAFLEX TM Pooling Bottle, manufactured and sold by Terumo Corporation (Japan).

*Primary Examiner*—Stephen C. Pellegrino
*Attorney, Agent, or Firm*—Paul C. Flattery; Bradford R. L. Price; Daniel D. Ryan

[57] ABSTRACT

A container for pooling plasma and the like has an integral cap. The cap includes an air vent with an inline bacterial filter. The cap also includes a fluid passage to which a length of tubing is integrally connected. The tubing includes at its unattached end one or more connector members which can be coupled to a fluid source to enable fluid to be transferred into the container via the tubing. The connector members are releasably secured to the cap prior to use. After fluid transfer is complete, the transfer tubing is sealed and severed close to the cap. The cap includes a pocket which receives the remaining sealed end portion of the tubing to protect the sealed end portion from inadvertent contact and damage during subsequent handling. The cover includes a plug which can be moved into a position which hermetically seals the vent and, thus, the entire container.

4 Claims, 15 Drawing Figures

FIG. 1 PRIOR ART
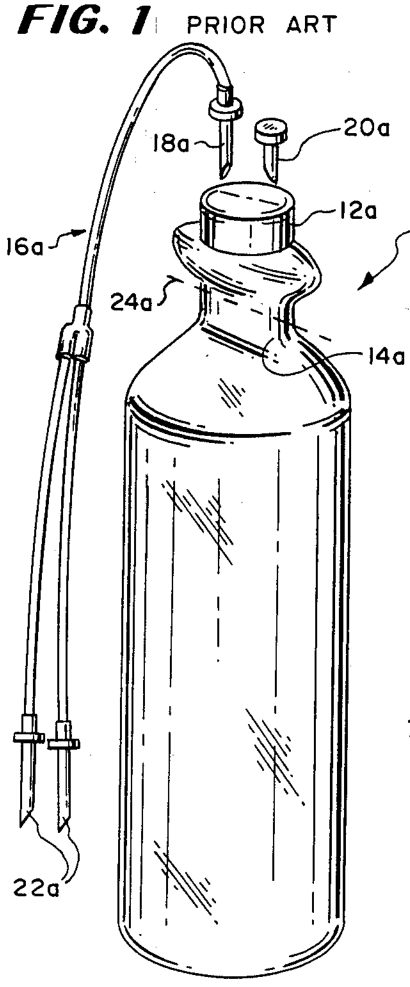
FIG. 2 PRIOR ART
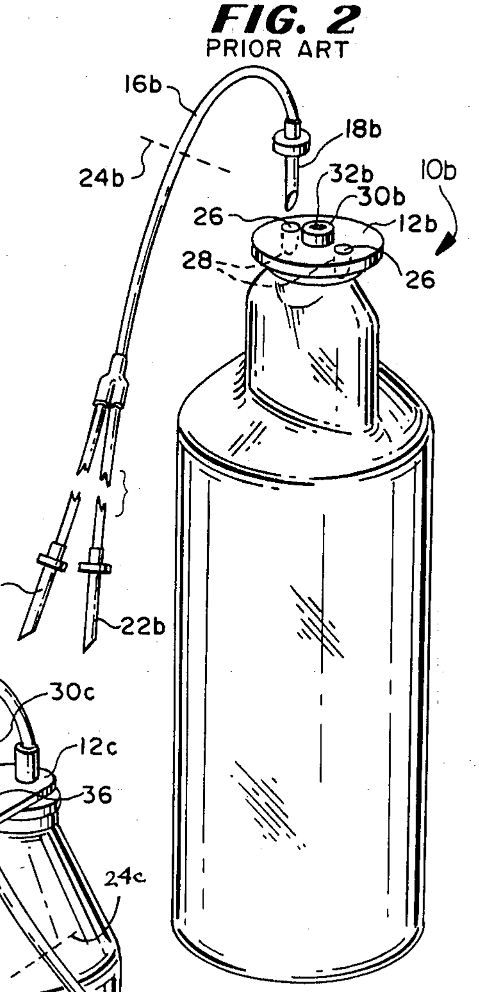
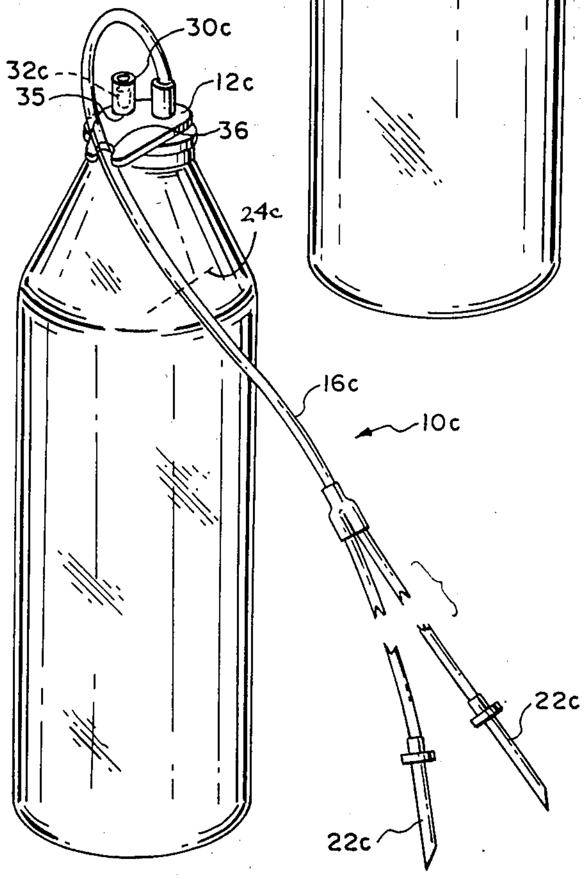
FIG. 3 PRIOR ART

CONTAINER AND ASSOCIATED CAP ASSEMBLY FOR PLASMA COLLECTION AND THE LIKE

RELATED APPLICATION

This application is a continuation-in-part of Keilman et al U.S. patent application Ser. No. 417,728, filed Sept. 13, 1982, now abandoned.

FIELD OF THE INVENTION

This invention generally relates to containers for liquid collection and, in particular, to containers for pooling plasma and other parenteral solutions.

THE BACKGROUND AND OBJECTS OF THE INVENTION

Plasmapheresis is a procedure which facilitates the collection of plasma for commercial fractionation into Clotting Factor VIII (also known as AHF), albumin, and other plasma-based protein fractions. During conventional plasmapheresis, a unit of whole blood is collected and separated into red blood cells and plasma. The red blood cells are returned to the donor, and the plasma is retained for fractionation purposes. Another unit of whole blood is then drawn from the same donor and again separated into red blood cells and plasma. Again, the red blood cells are returned to the donor, and only the plasma is retained.

Thus, two units of plasma can be obtained from a donor during a conventional plasmapheresis procedure. The two units of plasma are typically collected, or pooled, in a single container which has been specially designed for this purpose. The pooled plasma is frozen in the container and shipped to a fractionation facility. At the facility, the plasma is thawed and dumped from the container into a vat for fractionation.

A prior art plasma pooling container 10*a* is shown in FIG. 1. This container 10*a* is similar to one manufactured and sold by the Fenwal Division of Travenol Laboratories, Inc. (Deerfield, Illinois) as the PLASMA-GARD TM Plasma Pooling Bottle. The container 10*a* is manufactured from thermoplastic resins and includes an integral cap 12*a* and a narrow, constricted neck 14*a*. Plasma is transferred into the container 10*a* by use of a transfer set 16*a* having, at one end, a pointed spike 18*a* which is driven by the user through the cap 12*a*. To enable fluid transfer, a vent tube 20*a* is also driven by the user through the cap 12*a*. A pair of spikes 22*a* is situated at the other end of the transfer set 16*a*. Each spike 22*a* pierces a rupturable diaphragm located in the port of a bag (not shown) in which a unit of whole blood is collected and centrifugally separated into red blood cells and plasma. After the plasma of two collection bags has been pooled in the container 10*a*, the narrow, constricted neck 14*a* is cut generally along the line 24*a* to separate the cap 12*a*. At the same time, the neck 14*a* is sealed closed along the cutting line 24*a* by special heat sealing equipment to provide an air and fluid-tight seal for the container 10*a*.

A similar prior art pooling container (not shown) is disclosed in Shine et al U.S. Pat. No. 3,957,168. See also Shine et al U.S. Design Pat. DES No. 255,872.

Another prior art plasma pooling container 10*b* is shown in FIG. 2. This container 10*b* is similar to one manufactured and sold by Alpha Therapeutic Corporation (South Pasadena, California) and is generally disclosed in Safianoff U.S. Pat. No. 4,234,095. Like the container 10*a* just described, the container 10*b* is manufactured from a thermoplastic material and includes an integral cap 12*b*. Unlike the cap 12*a*, the cap 12*b* includes preformed sleeves 26 each of which defines a target for placement of the spike 18*b* associated with the plasma transfer set 16*b*. Each sleeve 26 also includes a preformed cylindrical guide 28 (shown in phantom lines in FIG. 2) which retains the inserted spike 18*b* in a tight interference fit. Also unlike the cap 12*a*, the cap 12*b* includes an integrally formed vent tube 30*b*. In this arrangement, after the plasma is pooled in the container 10*b*, the container 10*b* is closed by sealing and severing the tubing of the attached plasma transfer set 16*b* generally along the line 24*b*.

The resulting seal is fluid-tight. However, unlike the container 10*a*, the container 10*b* is not hermetically sealed, because the vent tube 30*b* is never closed. To maintain sterility in this arrangement, the vent tube 30*b* includes a plug 32*b* of sterile fibrous material.

Yet another prior art plasma pooling container 10*c* is shown in FIG. 3. This pooling container 10*c* is similar to one manufactured and sold by Terumo Corporation (Japan) as the PLASMAFLEX TM Pooling Bottle. This container 10*c* is also manufactured from a thermoplastic material and includes an integral cap 12*c*. An end of the transfer set 16*c* is integrally connected to one port 34 in the cap 12*c*, thereby eliminating the need for a spike. A vent tube 30*c* with a bacterial filter 32*c* (shown in phantom lines in FIG. 3) is provided in communication with another port 35 on the cap 12*c*. In this arrangement, the upper portion of the tubing is held relatively stationary by a holder 36. After the plasma has been collected, the upper portion tubing of the transfer set 16*c* is heat sealed closed and severed generally along the line 24*c*.

As with the bottle 10*b*, the resulting seal of the container 10*c* is fluid-tight, but it is not hermetic, because the vent tube 30*c* remains open.

Because the container 10*b* and 10*c* are not completely hermetically sealed, quick and efficient water bath immersion techniques cannot be used to thaw the plasma. Rather, more time-consuming techniques, such as shelf thawing or batch thawing, have to be utilized.

Furthermore, in both of the containers 10*b* and 10*c*, the sealed ends 24*b* and 24*c* of the associated transfer sets 16*b* and 16*c* are exposed to contact throughout freezing, shipping, and thawing operations. This tubing (typically made from a plasticized polyvinyl chloride material) can become brittle during exposure to low temperatures and can thus become even more vulnerable to being inadvertently broken or damaged as a result of contact. Should this occur, the sterile integrity of the frozen contents of the bottle 10*b* or 10*c* is, of course, compromised.

It should also be noted that, in both of the containers 10*a* and 10*b*, the associated transfer sets 16*a* and 16*b* constitute separate assemblies which must be coupled to the containers 10*a* and 10*b* at time of use. In the container 10*c* while one end of the transfer set 16*c* is integrally connected to the container 10*c*, the associated spikes 22*c* dangle from the container 10*c* prior to use. Thus, for various reasons, each of the containers 10*a*, 10*b*, and 10*c* poses handling and shipping problems.

With the foregoing considerations in mind, one of the principal objects of the invention is to provide a plasma pooling container or the like which comprises a compact unit which can be easily handled and transported both prior to and after the collection of fluid.

Another principal object of this invention is to provide a plasma pooling bottle or the like which serves to shield or protect the sealed end portion of associated tubing from being inadvertently broken or damaged during handling, thereby assuring that the sterile integrity of its contents is not compromised.

Yet another principal object of this invention is to provide a plasma pooling container or the like which can be hermetically sealed, thereby allowing complete water bath immersion of the container, if desired.

SUMMARY OF THE INVENTION

To achieve these and other objects, the invention provides a container assembly suited for the collection of plasma and other solutions. The container assembly includes an attached cap assembly which comprises a body through which a fluid path extends. The cap assembly also includes means for attaching one end of a length of tubing to the body in communication with the fluid path. The length of tubing includes at its opposite end connector means for coupling the tubing, and thus the container assembly, to a source of fluid.

In accordance with the invention, the cap assembly further includes means for releasably securing the connector means to the body of the cap assembly prior to use. The resulting assembly is compact and easy to handle. Damage to the connector means or accidental stretching or kinking of the associated tubing prior to use are also prevented.

In one embodiment, the cap assembly further includes means which defines in the body a pocket for selectively enclosing an end portion of the attached tubing after the end portion has been sealed closed to retain transferred fluids in the container.

Being enclosed in the pocket, the sealed end portion of the tubing is shielded from inadvertent contact, which can break or otherwise damage the end portion and compromise the sterile integrity of the contents of the container.

In one embodiment, the cap assembly also includes a vent for the associated container. In this embodiment, the cap assembly also preferably includes plug means movably attached on the body. When the plug means is in a first position, the vent is opened to permit the collection of fluid in the container. When the plug means is in a second position, it hermetically closes the vent and, thus, the container as well.

Other features and advantages of the invention will be pointed out in, or will be apparent from, the specification and claims, as will obvious modification of the embodiments shown in the drawings.

DESCRIPTION OF THE DRAWINGS

FIGS. 1 through 3 are perspective views of prior art plasma pooling bottles;

Before explaining the embodiments of the invention in detail, it is to be understood that the invention is not limited in this application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed are for the purpose of description and should not be regarded as limiting.

DESCRIPTION OF THE PREFERRED EMBODIMENTS

Figure 4:
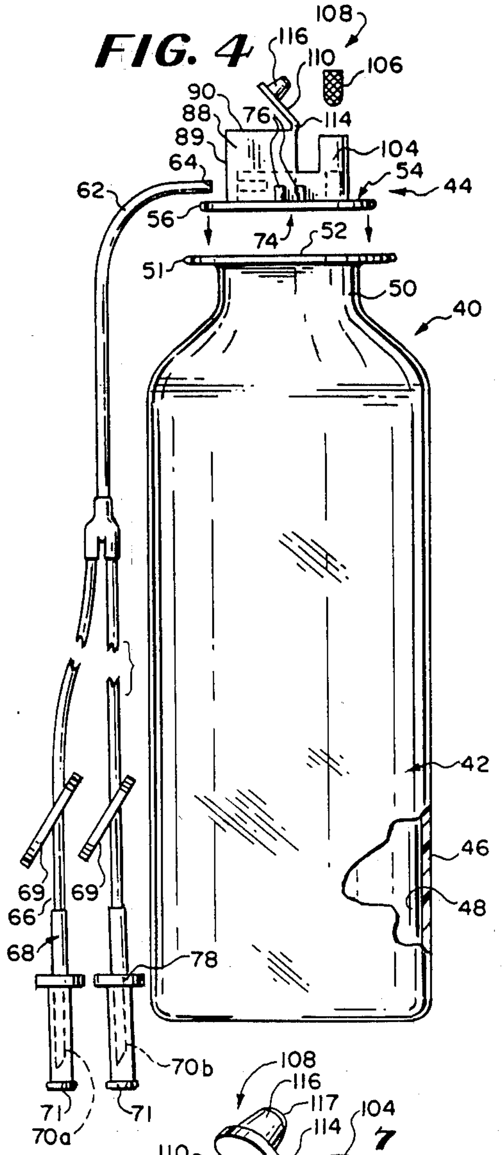
FIG. 4 is an exploded view, with a portion broken away and in section, of a container assembly which can be used as a plasma pooling bottle and which embodies the features of the invention.
Figure 5:
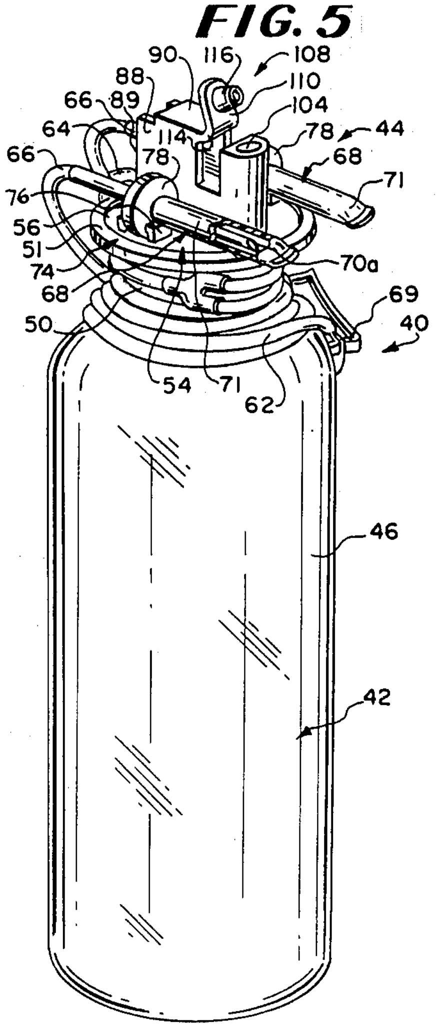
FIG. 5 is an assembled perspective view, with a portion broken away, of the container assembly shown in FIG. 4 prior to its use, with the associated vent passage open and the connectors, which are associated with the integrally attached transfer tubing, releasably secured to the cap assembly.

A container assembly 40 which embodies the features of the invention is shown in FIGS. 4 and 5. The assembly 40 includes a container 42 and a cap assembly 44 which is attached to the container 42, as shown in FIG. 5.

The container assembly 40 is particularly well-suited for collecting and pooling fluids, particularly in environments in which sterility is an important consideration both before and after collection. Because of this, the assembly 40 will be discussed in the context of the pooling of plasma for fractionation purposes. However, it should be appreciated that the assembly 40 is well-suited for use in other diverse operative environments.

The container 42 of the assembly 40 includes a body 46. The body 46 in the illustrated embodiment has a cylindrical, or bottle-like, configuration. However, other configurations may be used, depending upon the particular operative environment.

The body 46 peripherally defines an open interior 48 (see FIG. 4) for receiving fluids. The body 46 also includes a neck 50 having a port 52 which communicates with the open interior 48. A lip 51 peripherally encircles the port 52.

The container 42 may be variously constructed. In the illustrated embodiment, the container 42 is preferably made of a generally rigid, self-supporting plastic material which can be formed into the desired bottle-like shape utilizing conventional techniques, such as injection molding or blow molding. Other materials, such as glass or metal, could be also used, again depending upon the particular demands of the given operative environment.

In the illustrated embodiment, because the container 42 will be used for the collecting and pooling of plasma, the container body 46 is preferably made of a hemocompatible plastic having a relatively high low-temperature strength to withstand temperatures at or near −80° C., such as high density polyethylene or polypropylene. The pooled plasma can be frozen at these temperatures within the container interior 48 for shipment and storage prior to fractionation.

Also in the context of a plasma pooling container, the body 46 of the container 42 preferably has smooth interior walls to facilitate the removal of the plasma in frozen or semi-frozen form, if desired.

Figure 6:
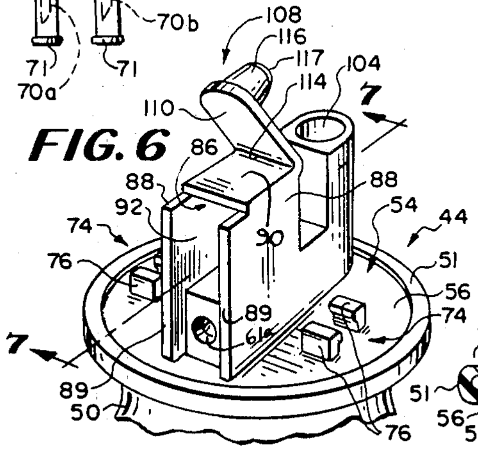
FIG. 6 is a perspective view of the cap assembly associated with the container assembly shown in FIG. 4.
Figure 7:
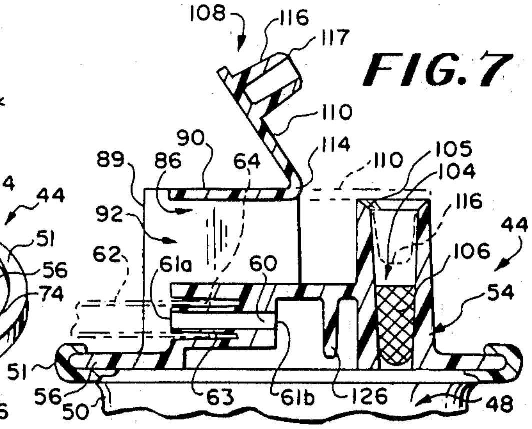
FIG. 7 is a side section view of the cap assembly taken generally along line 7—7 in FIG. 6.

As can be seen in FIGS. 4 through 7, the cap assembly 44 includes a body 54 which is operative for sealing engagement with the port 52 of the container 42. In the illustrated embodiment, as is best shown in FIG. 7, the cap body 54 includes a rim 56 over which the lip 51 of the container 42 is sealed to hermetically secure the cap body 54 to the container body 46.

As can also best be seen in FIG. 7, the cap assembly 44 further includes a fluid path 60 which extends through the body 54. When the cap body 54 is properly positioned on the neck 50 of the container 42, the path 60 communicates, at one end 61*a*, with the atmosphere and, at the other end 61*b*, with the interior 48 of the container 42.

A length of tubing 62 can be attached by various means to the cap body 54 in communication with the end 61*a* of the fluid path 60. The tubing 62 thus form an integrally connected part of the assembly 40 (see, in particular, FIGS. 4, 5, and 10).

In the illustrated embodiment, the tubing 62 is made of a thermoplastic, hemocompatible material, such as plasticized polyvinyl chloride. As shown in phantom lines in FIG. 7, one end 64 of the tubing 62 is sealingly secured to the end 61*a* of the fluid path 60. In the illustrated embodiment (see FIG. 7), a nipple 63 is formed at this end 61*a* of the fluid path 60 to form the connection site. The nipple 63 allows the connection to be made by an interference or friction fit.

The other end 66 of the tubing 60 (see, in particular, FIGS. 4 and 5) includes one or more connector means 68 for coupling the tubing 62, and thus the container assembly 10 itself, to an external source of fluid. It is this fluid which is then transferred, via the tubing 62, into the container 42. Convention flow control clamps 69 can be associated with the tubing 62, if desired.

The connector means 68 can be variously constructed and may be conventional in design. For example, in the embodiment shown in FIGS. 4, 5, and 9, the connection means 68 takes the form of a pair of conventional pointed spike members 70*a* and 70*b*. The spikes 70*a* and 70*b* are used in conventional fashion to penetrate membranes associated with the fluid source to open a fluid path into the container 42. Protective removable sheaths 71 are preferably provided for the spikes 70*a* and 70*b* to preserve their sterile integrity prior to use.

Figure 10:
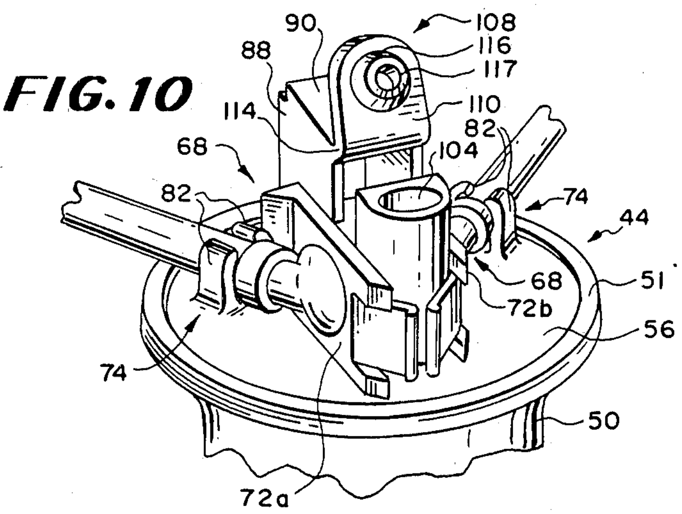
FIG. 10 is a perspective view of a cap assembly having connectors associated with the transfer tubing which are different than the connectors shown in FIG. 5 as well as alternate means for releasably securing these connectors to the cap assembly.

As shown in FIG. 10, in an alternate embodiment, the connection means 68 can include one or more sterile connectors 72*a* and 72*b*, such as disclosed in Granzow et al, U.S. Pat. Nos. 4,157,723, 4,265,280, or 4,340,097, which are all incorporated herein by reference.

As disclosed in the foregoing Granzow et al patents, by coupling these connectors 72*a* and 72*b* to matching connectors associated with the fluid source (not shown), a fluid path into the container 42 can be formed.

In accordance with an aspect of the invention, the cap assembly 44 further includes means 74 for releasably securing each of the associated connector means 68 to the cap body 54 prior to use.

The securing means 74 may be variously constructed, depending in large part upon the specific configuration of the associated connector means 68.

Figure 8:
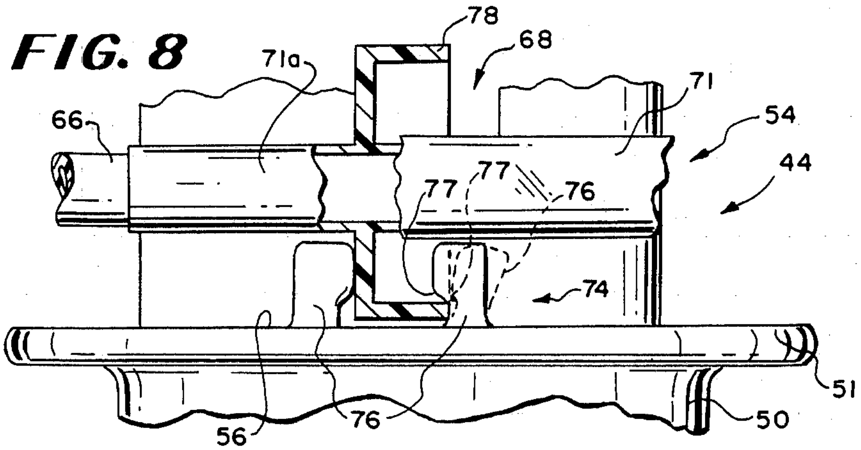
FIG. 8 is an enlarged side view, with a portion broken away and in section, of one of the connectors releasably secured to the cap assembly.

For example, in the embodiment shown in FIGS. 4 through 6, 8, and 9, the spike members 70*a* and 70*b* each include a collar 78 which projects radially outwardly of the tubular body of the spike 70*a* and 70*b*. In this arrangement, the connector means 68 includes, for each spike 70*a* and 70*b*, a spaced pair of upstanding shoulders 76 which project upwardly from the rim 56 of the cap body 54. As best shown in FIG. 8, the shoulders 76 are integrally molded on the cap body 54 and are each resiliently biased toward a perpendicular position relative to the plane of the rim 56. The shoulders 76 each includes a retainer portion 77 which, when the associated shoulder 76 is resilient moved out of its perpendicular position (as shown in phantom lines in FIG. 8), receives the rim of the collar 78 in a snap-fit fashion, as shown in solid lines in FIG. 8.

Figure 9:
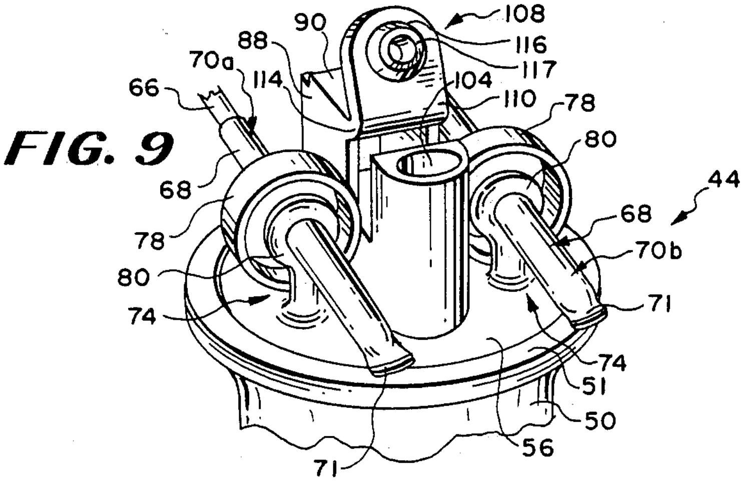
FIG. 9 is a perspective view of a cap assembly having an alternate means for releasably securing the connectors to the cap assembly.

In an alternate arrangement shown in FIG. 9, the connector means 68 includes, for each spike 70*a* and 70*b*, an upstanding hoop 80 which releasably receives the tubular body of the spike 70*a* and 70*b* in a tight interference fit.

In the embodiment shown in FIG. 10, the sterile connectors 72*a* and 72*b* are releasably secured between upstanding shoulders 82 identical in construction and operation to the shoulders 76 associated with the FIG. 8 embodiment.

Preferably, as shown in FIG. 5, prior to releasably securing the associated connector means 68 to the cap assembly 44 in any of the manners just described, the tubing 62 is wrapped around the neck 50 of the container 42, or otherwise coiled in close proximity to the container 42.

As shown in FIG. 5, prior to use, the assembly 40 constitutes a compact unit which can be easily handled, transported, and stored. Each of the connector means 68, being releasably secured on the cap assembly 44, is protected from inadvertant damage or separation prior to use. The coiled tubing 62 is also protected from being stretched, kinked, or twisted.

Like the container body 46, the body 54 of the cap assembly 44 may be variously constructed. However, in the illustrated embodiment, the body 54 is made of a plastic material formed into the desired shape by conventional means, such as by injection molding. The body material is preferably compatible with the plastic material used for the container 42, so that the rim 56 of the cap body 54 may be sealingly secured on the container neck portion 50 by heat sealing, sonic molding, spin welding, or the like.

Preferably, the material for the cap body 54 is also compatible with polyvinyl chloride plastic, so that the end 64 of the polyvinyl chloride tubing 62 can be solvent bonded to the end 61*a* of the fluid path 60. A secure, integral connection between the cap body. 54 and the tubing 62 is thus possible. Alternately, as shown in the embodiment illustrated in FIG. 7, the nipple 63 is provided so that a sure mechanical bond between the tubing end 64 and the fluid path end 61*a* can be created.

In the illustrated embodiment, the cap body 54 is made from a high density polyethylene. Alternately, the cap body 54 can be made of a preselected blend of plastics which include from 50 to 75 percent by weight a polyolefin material and from 25 to 50 percent by weight of a flexible block copolymer of covalently bonded polybutylene terephthalate units and poly(1,4-butylene) oxide units. Such a blend is disclosed in Kwong et al U.S. Pat. No. 4,327,726, which is incorporated herein by reference.

Both plastic materials can be sonic welded to high density polyethylene.

The blended plastic material is also readily solvent bondable to the polyvinyl chloride tubing 62.

Figure 12:
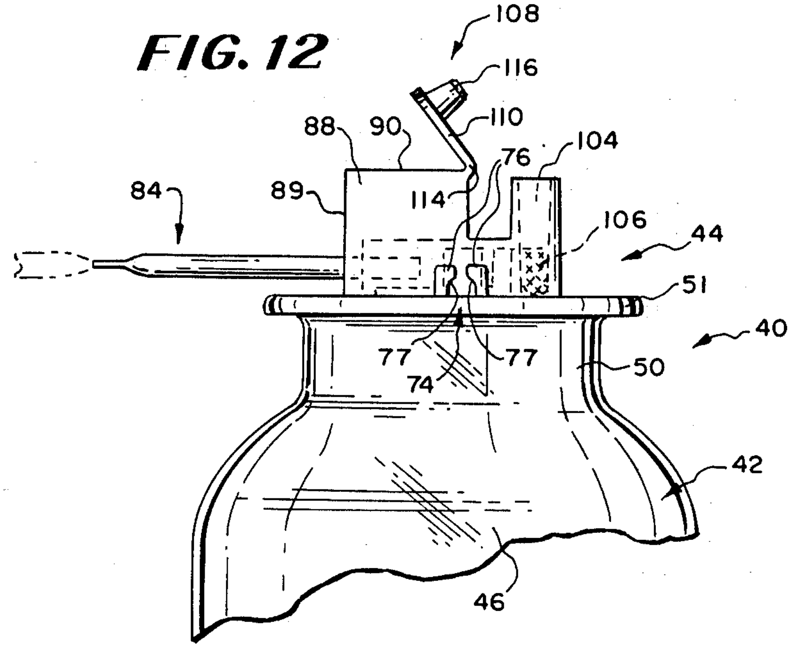
FIG. 12 is an elevation view of the cap assembly of the container assembly shown in FIG. 5, after the associated transfer tubing has been heat sealed closed and severed.

In the particular operative environment of the illustrated embodiment, as shown in FIG. 12, after plasma has been introduced into the container 42, the end 66 of the tubing 62, and with it both spike members 70*a* and 70*b* (or other associated connector means 68) are separated from the container assembly 40. The tubing 62 will also be sealed at the point of separation, leaving a sealed end portion 84 attached to the cap body 54. This portion 84 provides a fluid-tight seal for the assembly 40.

It is highly desirable to protect the sealed end portion 84 from inadvertent damage during subsequent handling of the assembly 40. Such damage could compromise the fluid-tight seal and jeopardize the sterile integrity of the contents of the container 42.

Therefore, as is best shown in FIGS. 6 and 7, the cap assembly 44 includes means defining a pocket 86 in the body 54 for therein selectively enclosing the sealed end portion 84 of the attached tubing 62.

The pocket 86 may be variously configured and located on the cap body 54. In the illustrated embodiment, as best shown in FIGS. 6 and 7, the pocket 86 extends above the rim 56 axially of the fluid path 60.

More particularly, the pocket 86 is peripherally bounded by a pair of upstanding sidewalls 88 and an overlying top 90. The pocket 86 includes oppositely spaced open ends 92 and 94 (see FIG. 7). The open end 92 is disposed adjacently above the end 61*a* of the fluid path 60 to which the tubing 62 is attached. As shown in FIGS. 6 and 7, the edges 89 of the sidewalls 88 preferably extend outwardly beyond the end 61*a* of the fluid path 60.

Figure 13:
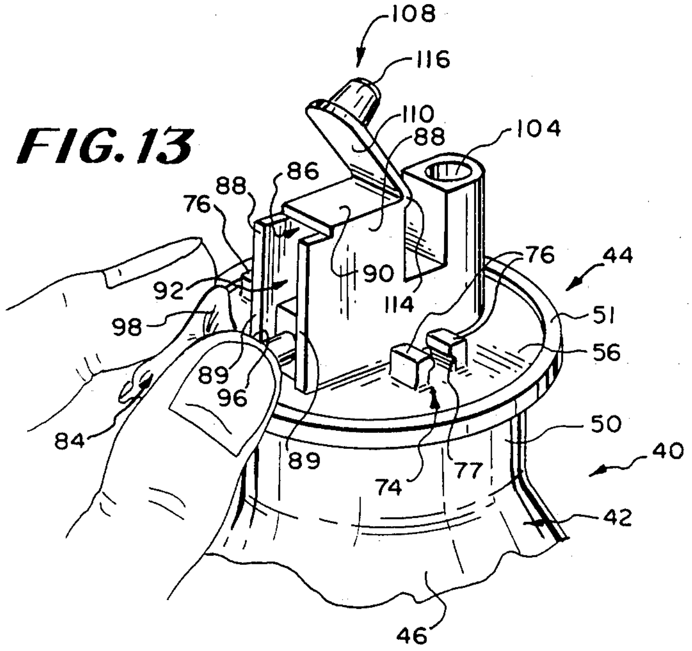
FIG. 13 is a perspective view of the cap assembly shown in FIG. 12 with the sealed tubing end being laid back upon itself by the attendant prior to its insertion into the protective pocket of the cap assembly.
Figure 14:
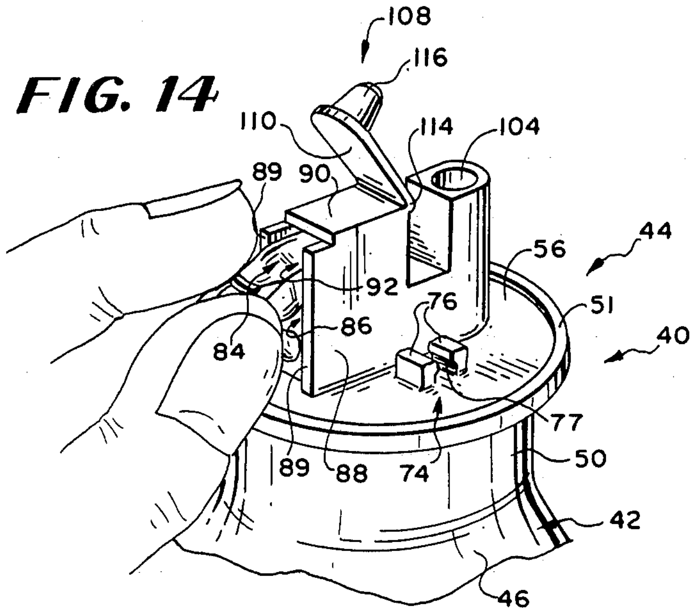
FIG. 14 is a perspective view of the cap assembly shown in FIG. 12 with the sealed tubing end being inserted into the protective pocket.
Figure 15:
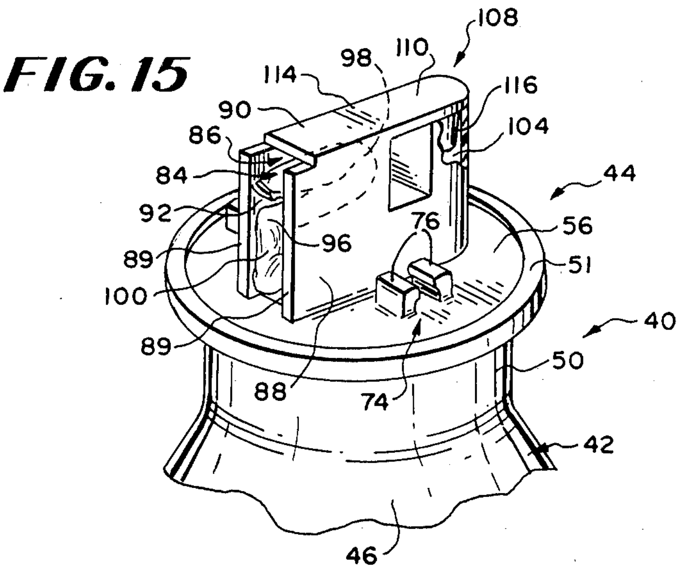
FIG. 15 is a perspective view of the cap assembly shown in FIG. 12 showing the sealed tubing end lodged in the protective pocket and the associated vent passage closed.

As can be seen sequentially in FIGS. 13 through 15, the sealed end portion 84 can be bent back through open end 92 and laid into the pocket 86. As can be seen in FIG. 15, this backward bending movement forms a crimp 96, or occlusion, in the tubing 84 as it extends through the open end 92. This crimped portion 96 serves as an additional fluid-tight seal which supplements the already formed fluid-tight seal at the tubing end 84.

As can be seen in FIG. 15, the section 100 of tubing 84 which extends between the end 61*a* of the fluid path and the crimped portion 96 is generally shielded from exterior contact by the outwardly extended sidewall edges 89.

Depending upon the length of the sealed end portion 84, a second crimp 98 can also be formed in the portion 84 disposed in the tubing pocket 86.

The interior of the pocket 86 is preferably sized to accommodate the sealed end portion 84 of the tubing 62 in a tight, friction fit. The end portion 84 of the plasticized tubing 62 can thus be tightly and securely lodged within the pocket 86 in the manner shown in FIG. 15.

The cap assembly 44 also includes vent means 104 which, in the illustrated embodiment, takes the form of a generally vertically disposed passage extending through the cap body 54 adjacent to the pocket 86.

A filter member 106 (see FIGS. 4, 7, and 12) is preferably press-fitted within the vent passage 104. The filter member 106 permits the passage of air, but blocks the passage of bacteria. The sterility of the interior 48 of the container 42 is thus maintained.

While the filter member 106 may be variously constructed, in the illustrated embodiment, it takes the form of a plug of a sintered microporous polyethylene available under the trademark "POREX" from Porex Technologies of Fairburn, Georgia.

The cap assembly 44 also preferably includes plug means 108 which is movable relative to the cap body 54 between a first position (shown in FIGS. 4 through 14), which opens the vent passage 104, and a second position (shown in FIG. 15 and in phantom lines in FIG. 7), which closes the vent passage 104.

While the plug means 108 may be variously constructed, in the illustrated embodiment, the plug means 108 includes a resilient, generally flat tab member 110 which extends outwardly beyond one edge of the overlying pocket top 90.

The plug means 108 further includes a plastic hinge portion 114 which flexibly joins the tab member 110 to the edge of the pocket cover 90. The tab member 110 can thus be moved relative to the first body 54 between the heretofore described first and second positions.

Preferably, the hinge portion 114 resiliently biases the tab member 110 toward the first, or opened, position.

The plug means 108 also includes a plug member 116 disposed at the outermost end of the tab member 110. The plug member 116 is positioned to engage the vent passage 104 when the tab member 110 is placed into its second position (as shown in FIG. 15 and in phantom lines in FIG. 7).

Preferably, the plug member 116 makes a hermetic interference fit within the vent passage 104. As best shown in FIG. 7, the interior of the vent passage 104 and the exterior of the plug member 116 can be correspondingly tapered to promote this interference fit and the resulting hermetic seal.

Furthermore, as is shown in FIG. 7, the leading edge 117 of the plug member 116 and the entrance 105 of the vent passage 104 can be correspondingly beveled to assure proper registry between the two as the tab member 110 is moved toward its closed position.

Reference is now made to FIGS. 11 through 15, which illustrate the use of the just described container assembly 40 in the context of a typical plasma pooling procedure.

Figure 11:
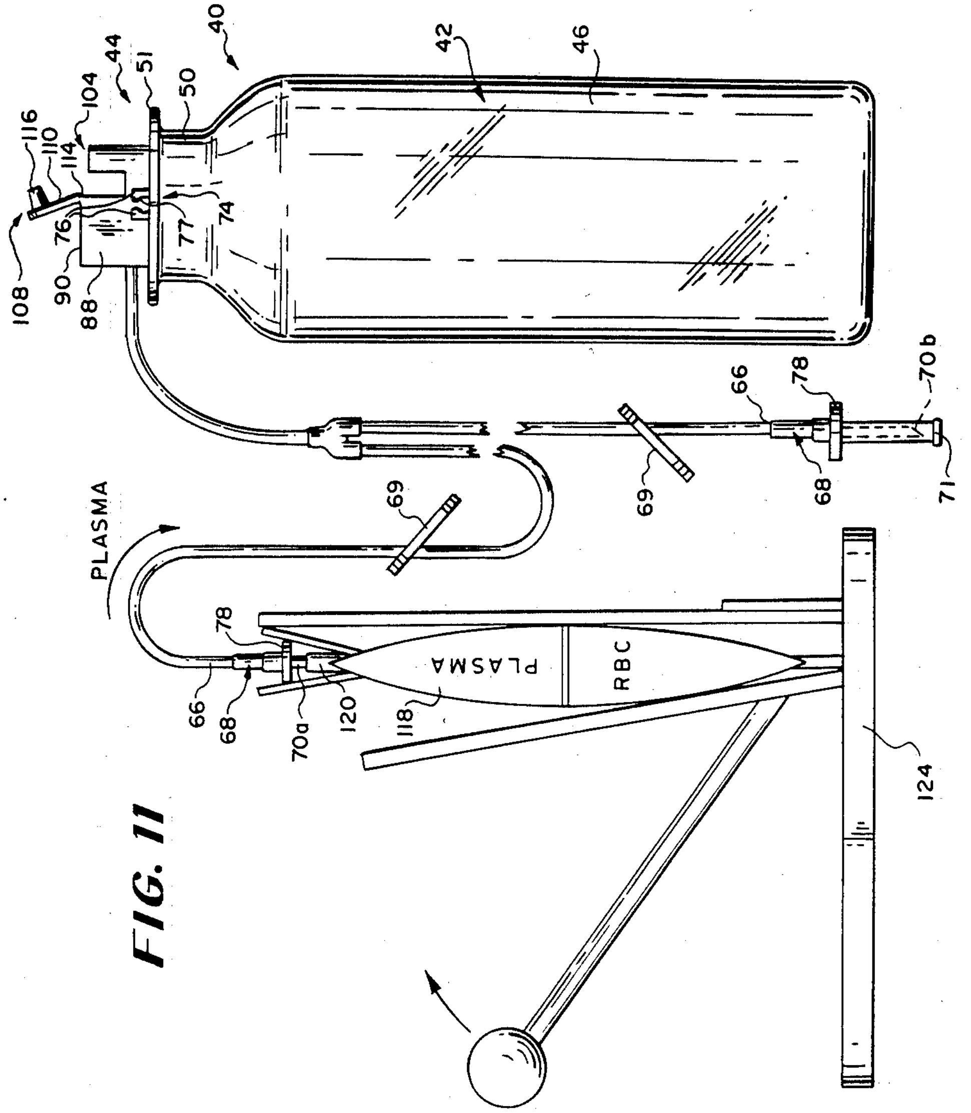
FIG. 11 is an elevation view of the container assembly shown in FIG. 5 in use, with one of the connectors coupled to a blood collection bag and plasma being transferred from the bag into the assembly through the associated transfer tubing.

During conventional plasmapheresis, a unit of whole blood is collected in a bag 118 (see FIG. 10) which is centrifuged to separate the whole blood into red blood cells (abbreviated RBC in FIG. 11) and plasma. As shown in FIG. 11, the connector means 68 (which are shown to be the spikes 70*a* and 70*b*) are released from the securing means 74, and the tubing 62 is uncoiled. The tab member 110 is situated in its normally biased first position to open the vent passage 104. One spike member 70*a* of the transfer set tubing 62 is inserted into an outlet port 120 of the bag 118. The spike member 70*a* pierces through a membrane (not shown) which normally closes the outlet port 120. The plasma is expressed into the interior 48 of the container 42 by using, for example, a manual plasma expelling device 124.

As shown in FIG. 7, a downwardly depending deflector 126 can be placed a short distance from the opening 61*b* to deflect the the incoming flow of plasma away from the filter member 106. This prevents wetting of the filter member 106.

The red blood cells remaining in the bag 118 are then returned to the donor.

Typically, another unit of whole blood is collected from the same donor into another bag (not shown) and centrifugally separated into red blood cells and plasma. The second unit of plasma is expressed into the container 42 using the second spike member 70*b*. The remaining red blood cells are again returned to the donor.

Upwards to about 700 milliliters of plasma can be pooled from a single donor into the container 42 using this procedure. The container interior 48 is sized to comfortably accommodate this maximum anticipated volume.

As shown in FIG. 12, after the two units of plasma have been pooled in the container 42, the transfer tubing 62 is hermetically sealed closed and severed as close as possible to the cap body 54. A HEMATRON® dielectric sealer manufactured and sold by the Fenwal Division of Travenol Laboratories, or a comparable dielectric sealer, can be used for this purpose.

The sealed end portion 84 remains attached to the cap body 54, as previously described and shown in FIG. 12.

As shown in FIG. 13, the sealed end portion 84 can be laid back upon itself, forming the heretofore described crimp or crimps 96 and 98. As shown in FIG. 14, this laid back portion 84 can then be pressed into the pocket 86, where it is securely retained by virtue of the friction fit, as shown in FIG. 15.

As shown in FIG. 15, the tab member 110 can now be moved into its second, or closed, position, thereby moving the plug member 116 into the vent passage 104. This hermetically seals the vent passage 104, and thus the entire assembly 40.

With the cap assembly 44 situated as shown in FIG. 15, the container assembly 40 can be frozen, shipped, stored, and processed as a compact, hermetically sealed unit.

Because the sealed end portion 84 remains enclosed within the confines of the pocket 86, it is effectively shielded during subsequent handling from inadvertent damage.

Furthermore, because the vent passage 104 remains hermetically sealed during subsequent handling, the container assembly 40 can undergo complete water bath immersion to thaw the plasma quickly and completely in a relatively short period of time.

The invention thus serves to protect the sterile integrity of the container assembly 40 during handling. At the same time, the invention facilitates faster and more efficient fractionation procedures.

Various of the features of the invention are set forth in the following claims.

We claim:

1. A container assembly for pooling plasma and other parenteral fluids comprising
- a container having an interior and a port communicating with the interior, and
- a cap including
  - a body engaged with said container port,
  - means for defining a fluid path through said body means communicating with the atmosphere and with said container interior,
  - a length of tubing attached at one end to said body in communication with said fluid path, said tubing having an initial length in which said tubing includes at its other end connector means for coupling said tubing in fluid communication with a fluid source to introduce fluids into said container interior,
  - means for releasably securing said connector means on said cap body,
  - said tubing adapted for being subsequently sealed and severed, forming a sealed end portion of said attached tubing, in close proximity to said one tubing end, and
  - means defining a pocket in said body for therein selectively enclosing said sealed end portion.

2. A cap assembly comprising
- a body
- means for defining a fluid path through said body,
- means for attaching one end of a length of tubing to said body in communication with said fluid path, said length of tubing having an initial length in which said tubing includes at its unattached end connector means for coupling said tubing in fluid communication with a fluid source,
- means for releasably securing said connector means on said cap body,
- said tubing adapted for being subsequently sealed and severed, forming a sealed end portion of said attached tubing, in close proximity to said one tubing end, and
- means defining a pocket in said body for therein selectively enclosing said sealed end portion.

3. A container assembly for pooling plasma and other parenteral fluids comprising
- a container having an interior and a port communicating with the interior, and
- a cap including
  - a body engaged with said container port,
  - means for defining a fluid path through said body means communicating with the atmosphere and with said container interior,
  - a length of tubing attached at one end to said body in communication with said fluid path, said tubing having an initial length in which said tubing includes at its other end connector means for coupling said tubing in fluid communication with a fluid source to introduce fluids into said container interior,
  - means for releasably securing said connector means on said cap body,
  - said tubing adapted for being subsequently sealed and severed, forming a sealed end portion of said attached tubing, in close proximity to said one tubing end, and
  - means defining a pocket in said body operative for receiving said sealed end portion in a friction fit to retain said sealed end portion in said pocket means.

4. A cap assembly comprising a body means for defining a fluid path through said body, means for attaching one end of a length of tubing to said body in communication with said fluid path, said length of tubing having an initial length in which said tubing includes at its unattached end connector means for coupling said tubing in fluid communication with a fluid source, means for releasably securing said connector means on said cap body, said tubing adapted for being subsequently sealed and severed, forming a sealed end portion of said attached tubing, in close proximity to said one tubing end, and means defining a pocket in said body operative for receiving said sealed end portion in a friction fit to retain said sealed end portion in said pocket means.

* * * * *